(12) United States Patent
Stewart et al.

(10) Patent No.: US 10,258,479 B2
(45) Date of Patent: Apr. 16, 2019

(54) DEVICES, METHODS, AND SYSTEMS TO IMPLANT AND SECURE A FUSION CAGE OR INTERVERTEBRAL PROSTHESIS FOR SPINAL TREATMENT

(71) Applicant: LDR Medical, Rosières Près Troyes (FR)

(72) Inventors: Will Stewart, Cedar Park, TX (US); Guillaume Quetier, Austin, TX (US); James Burrows, Marble Falls, TX (US)

(73) Assignee: LDR Medical, Rosieres Pres Troyes (FR)

( * ) Notice: Subject to any disclaimer, the term of this patent is extended or adjusted under 35 U.S.C. 154(b) by 105 days.

(21) Appl. No.: 14/827,297

(22) Filed: Aug. 15, 2015

(65) Prior Publication Data
US 2017/0042692 A1    Feb. 16, 2017

(51) Int. Cl.
*A61F 2/44* (2006.01)
*A61F 2/46* (2006.01)
(Continued)

(52) U.S. Cl.
CPC .............. *A61F 2/442* (2013.01); *A61B 17/92* (2013.01); *A61F 2/30749* (2013.01);
(Continued)

(58) Field of Classification Search
CPC ... A61B 17/7076; A61B 17/92; A61B 17/921; A61B 2017/922; A61B 2017/924;
(Continued)

(56) References Cited

U.S. PATENT DOCUMENTS

| | | | | |
|---|---|---|---|---|
| 3,366,187 A | * | 1/1968 | Von Tersch | B25B 19/00 173/93.6 |
| 3,837,410 A | * | 9/1974 | Maxwell | B23B 45/00 173/109 |

(Continued)

FOREIGN PATENT DOCUMENTS

| | | |
|---|---|---|
| CN | 108430359 A | 8/2018 |
| DE | 3802033 C1 | 6/1989 |

(Continued)

OTHER PUBLICATIONS

"International Application Serial No. PCT/EP2016/069454, International Preliminary Report on Patentability dated Mar. 1, 2018", 6 pgs.

(Continued)

*Primary Examiner* — Lynnsy M Summitt
(74) *Attorney, Agent, or Firm* — Schwegman Lundberg & Woessner, P.A.

(57) ABSTRACT

Various devices, methods, and systems to implant and secure a fusion cage or intervertebral prosthesis during treatment of spinal injury or disease are provided. In various embodiments, such devices may comprise an instrument assembly having a body comprising a head, a shaft, and a handle; an insertion stop; and an intervertebral device retainer. Various embodiments also may comprise an impactor assembly comprising a housing; a bit comprising a head, a shaft, and a coupler; a transmission comprising a housing, a cam, a cam follower, a collet, and a driveshaft; and the motor. In various embodiments, the impactor assembly may be deployed with adjustments for the frequency, displacement, and force of impulses delivered to an anchor for the intervertebral device.

19 Claims, 14 Drawing Sheets

(51) Int. Cl.
*A61F 2/30* (2006.01)
*A61B 17/92* (2006.01)

(52) U.S. Cl.
CPC .......... *A61F 2/4455* (2013.01); *A61F 2/4611* (2013.01); *A61F 2/447* (2013.01); *A61F 2002/4475* (2013.01); *A61F 2002/4623* (2013.01); *A61F 2220/0016* (2013.01)

(58) Field of Classification Search
CPC ........ A61B 2017/925; A61B 2017/927; A61B 2017/928; A61F 2002/4625; A61F 2002/4668; A61F 2002/4658; A61F 2002/4659; A61F 2002/4661; A61F 2002/4662; A61F 2002/4663; A61F 2002/4664; A61F 2002/4627; A61F 2/46; A61F 2/4611; A61F 2/4603; A61F 2/4684; A61F 2/4657
See application file for complete search history.

(56) References Cited

U.S. PATENT DOCUMENTS

| | | | | |
|---|---|---|---|---|
| 4,030,556 | A * | 6/1977 | Phillips | B25D 11/108 173/120 |
| 4,082,152 | A * | 4/1978 | Whitworth | B25D 11/102 172/123 |
| 6,785,950 | B1 * | 9/2004 | Scirbona | B25D 11/102 173/203 |
| 8,333,804 | B1 * | 12/2012 | Wensel | A61B 17/864 623/17.11 |
| 8,343,219 | B2 * | 1/2013 | Allain | A61B 17/0642 606/100 |
| 8,460,388 | B2 * | 6/2013 | Kirwan | A61F 2/4455 623/17.11 |
| 9,039,774 | B2 * | 5/2015 | Chataigner | A61F 2/442 623/17.16 |
| 9,044,337 | B2 * | 6/2015 | Dinville | A61F 2/447 |
| 2012/0078371 | A1 * | 3/2012 | Gamache | A61F 2/4465 623/17.16 |
| 2012/0078373 | A1 * | 3/2012 | Gamache | A61B 17/8625 623/17.16 |
| 2012/0265259 | A1 | 10/2012 | Laposta et al. | |
| 2013/0166029 | A1 | 6/2013 | Dinville et al. | |
| 2013/0204264 | A1 | 8/2013 | Mani et al. | |
| 2013/0226300 | A1 * | 8/2013 | Chataigner | A61F 2/442 623/17.16 |
| 2013/0245767 | A1 | 9/2013 | Lee et al. | |
| 2013/0261681 | A1 | 10/2013 | Bittenson | |
| 2014/0114413 | A1 | 4/2014 | Allain et al. | |
| 2015/0127107 | A1 * | 5/2015 | Kim | A61F 2/447 623/17.16 |
| 2015/0196343 | A1 * | 7/2015 | Donald | A61B 17/92 606/100 |
| 2015/0209089 | A1 * | 7/2015 | Chataigner | A61B 17/7064 623/17.16 |
| 2016/0058564 | A1 * | 3/2016 | Zappacosta | A61F 2/4455 623/17.16 |
| 2016/0058565 | A1 * | 3/2016 | Zappacosta | A61F 2/4455 623/17.16 |
| 2018/0235767 | A1 | 8/2018 | Stewart et al. | |

FOREIGN PATENT DOCUMENTS

| | | |
|---|---|---|
| EP | 0617926 A2 | 10/1994 |
| EP | 3334357 | 6/2018 |
| WO | WO-8802246 A2 | 4/1988 |
| WO | WO-2010121028 A2 | 10/2010 |
| WO | WO-2013062716 A1 | 5/2013 |
| WO | WO-2017029301 A1 | 2/2017 |

OTHER PUBLICATIONS

"International Application Serial No. PCT/EP2016/069454, International Search Report dated Dec. 1, 2016", 5 pgs.
"International Application Serial No. PCT/EP2016/069454, Written Opinion dated Dec. 1, 2016", 4 pgs.
"European Application Serial No. 16762736.3, Response filed Oct. 8, 2018 to Communication pursuant to Rules 161(1) and 162 EPC dated Mar. 28, 2018", 6 pgs.

* cited by examiner

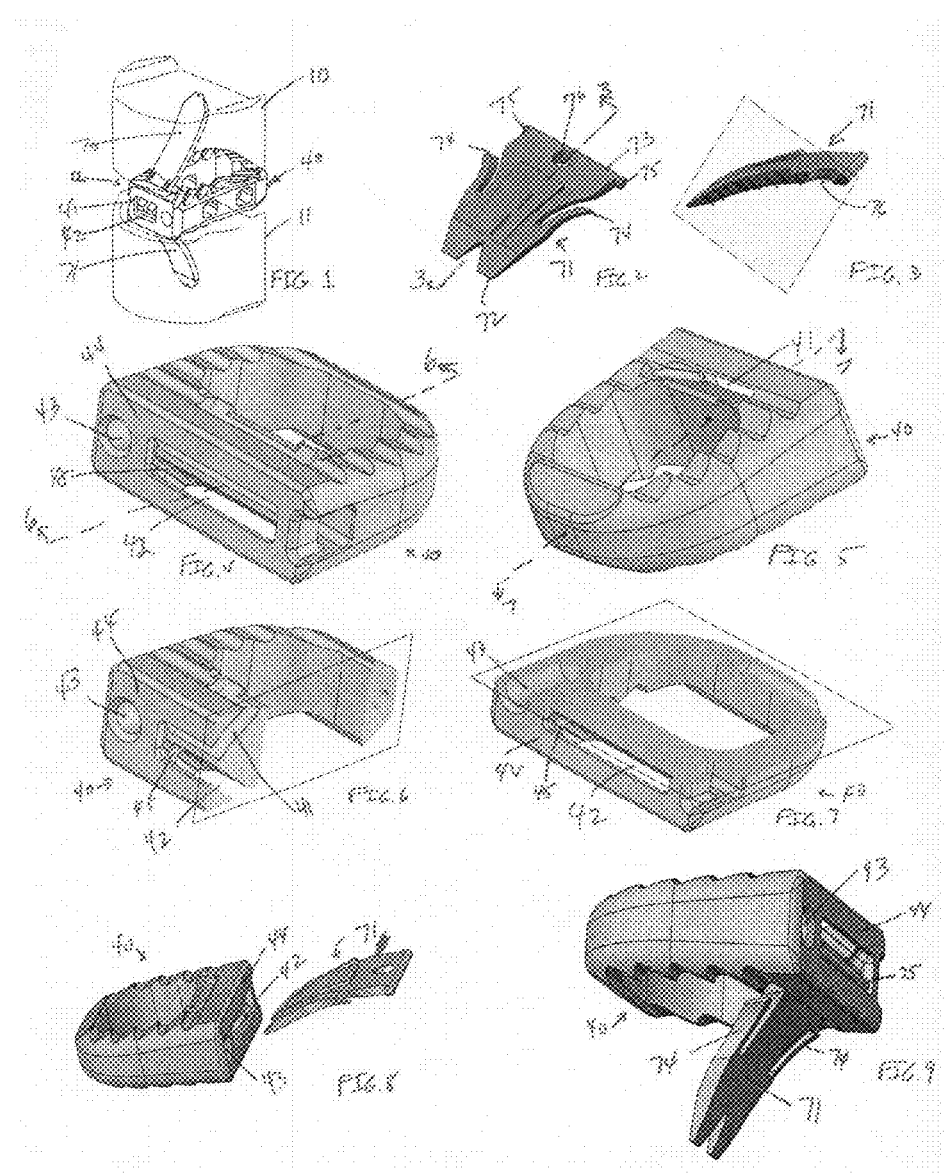

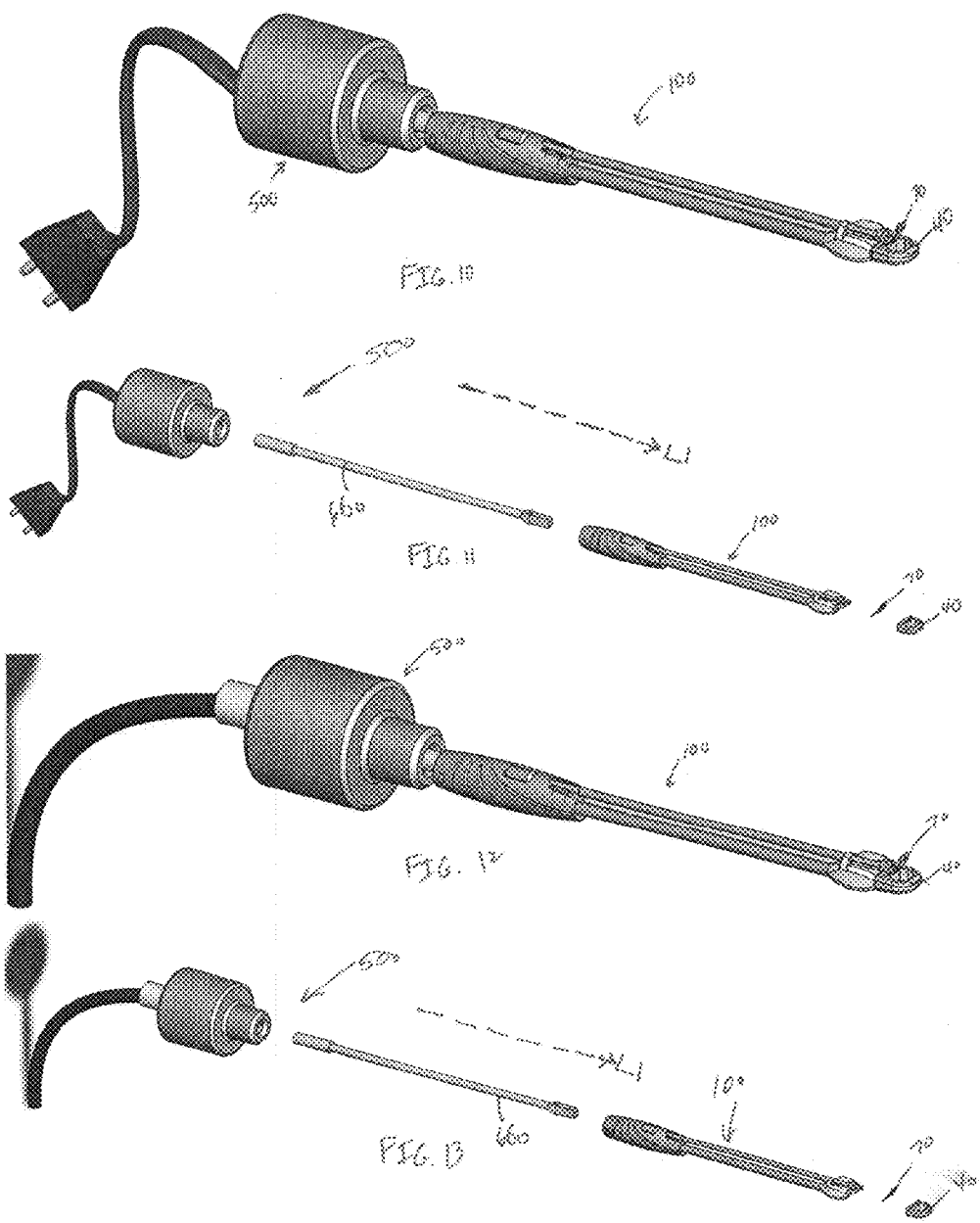

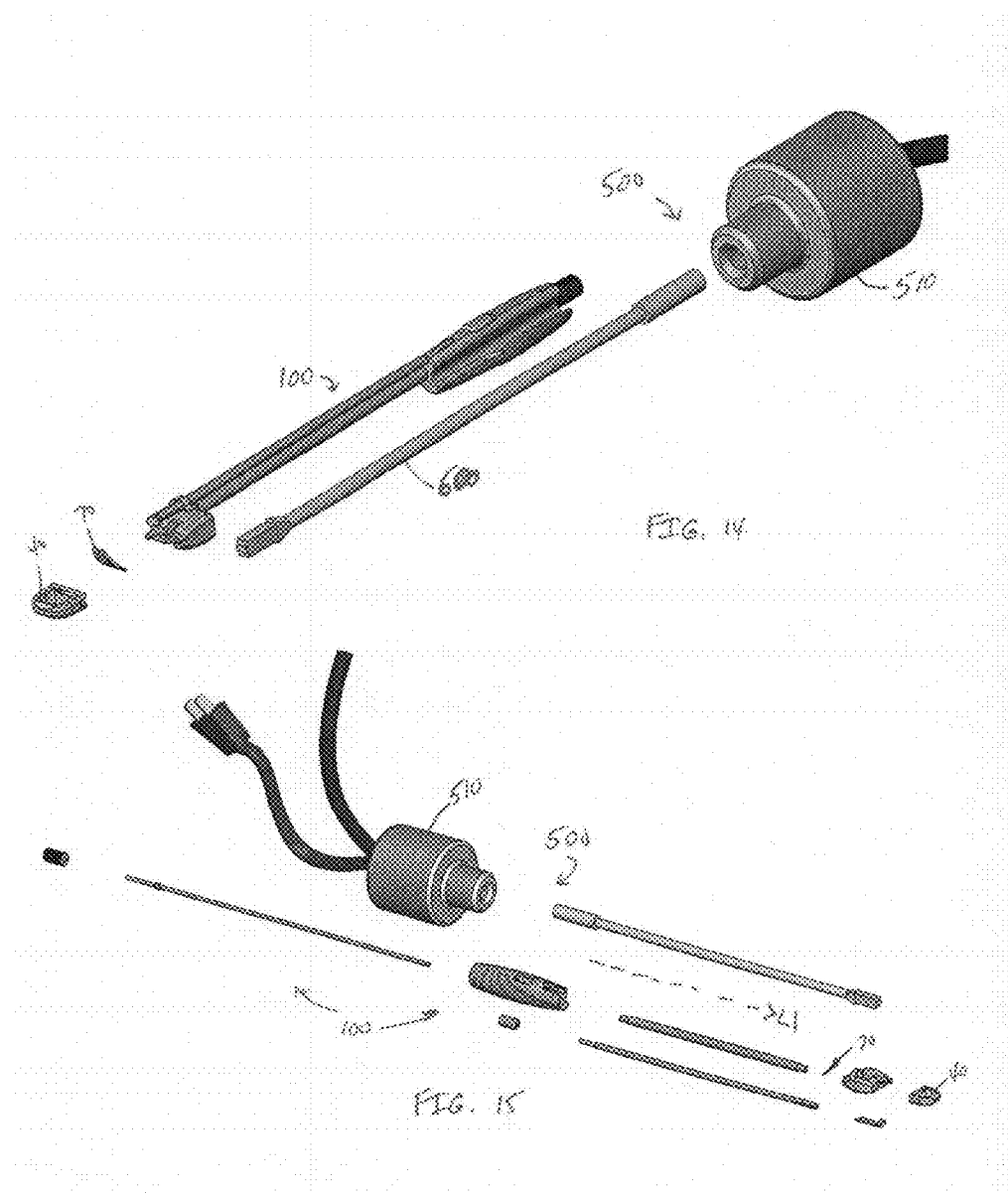

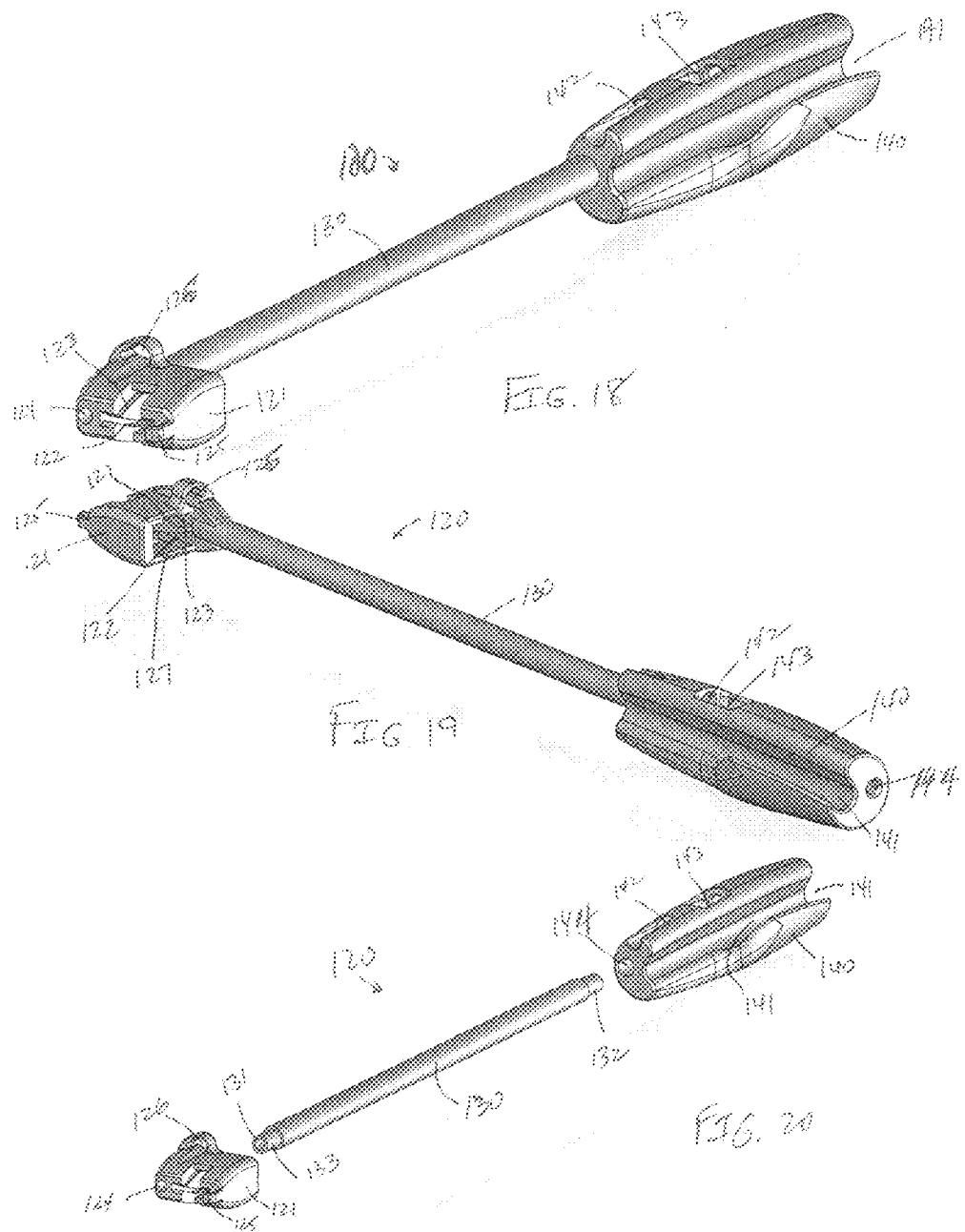

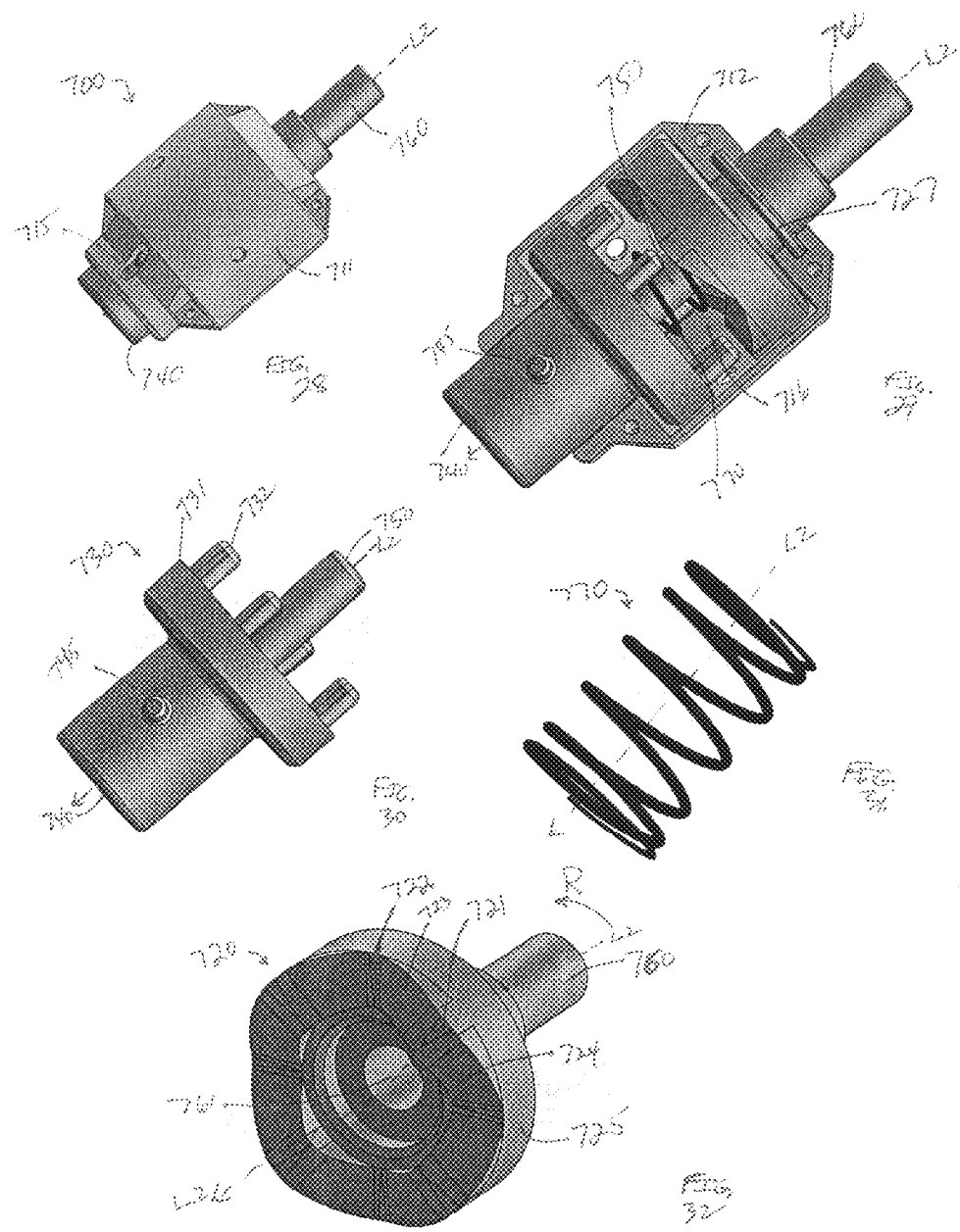

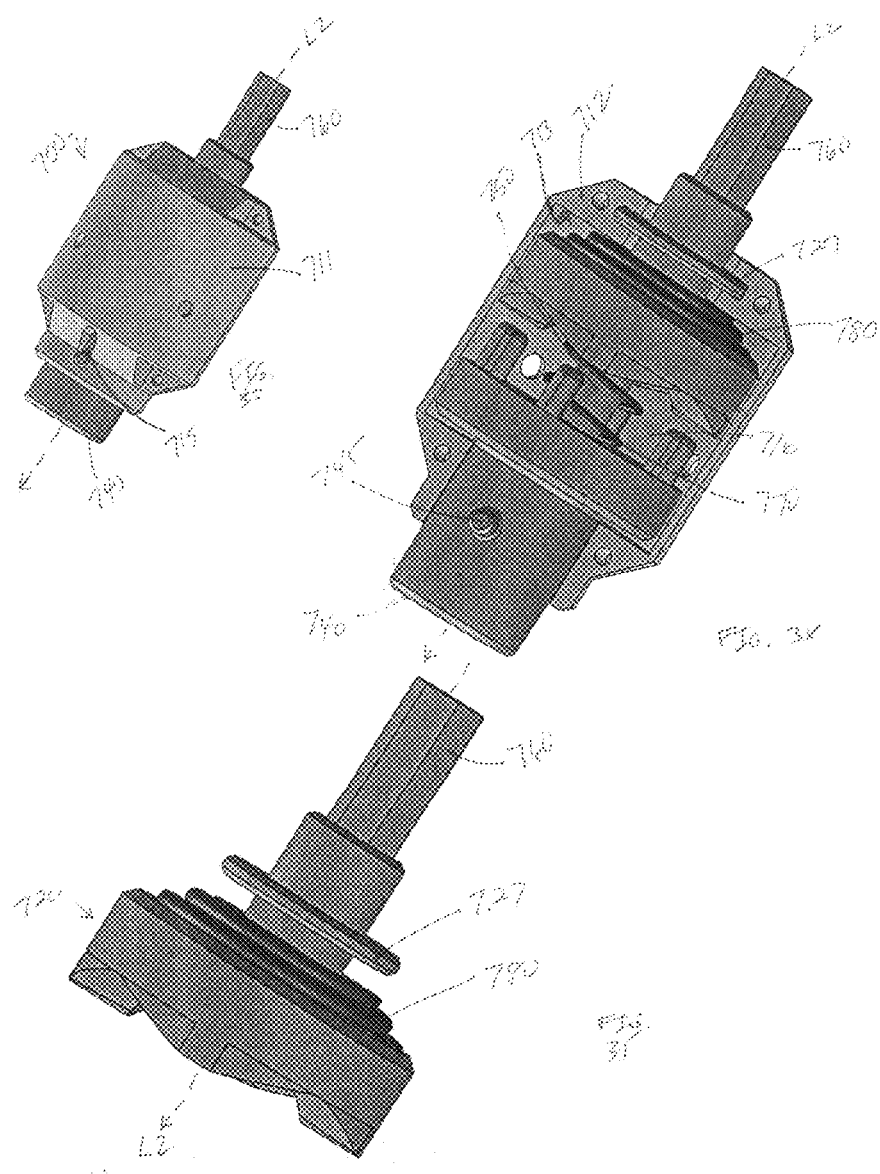

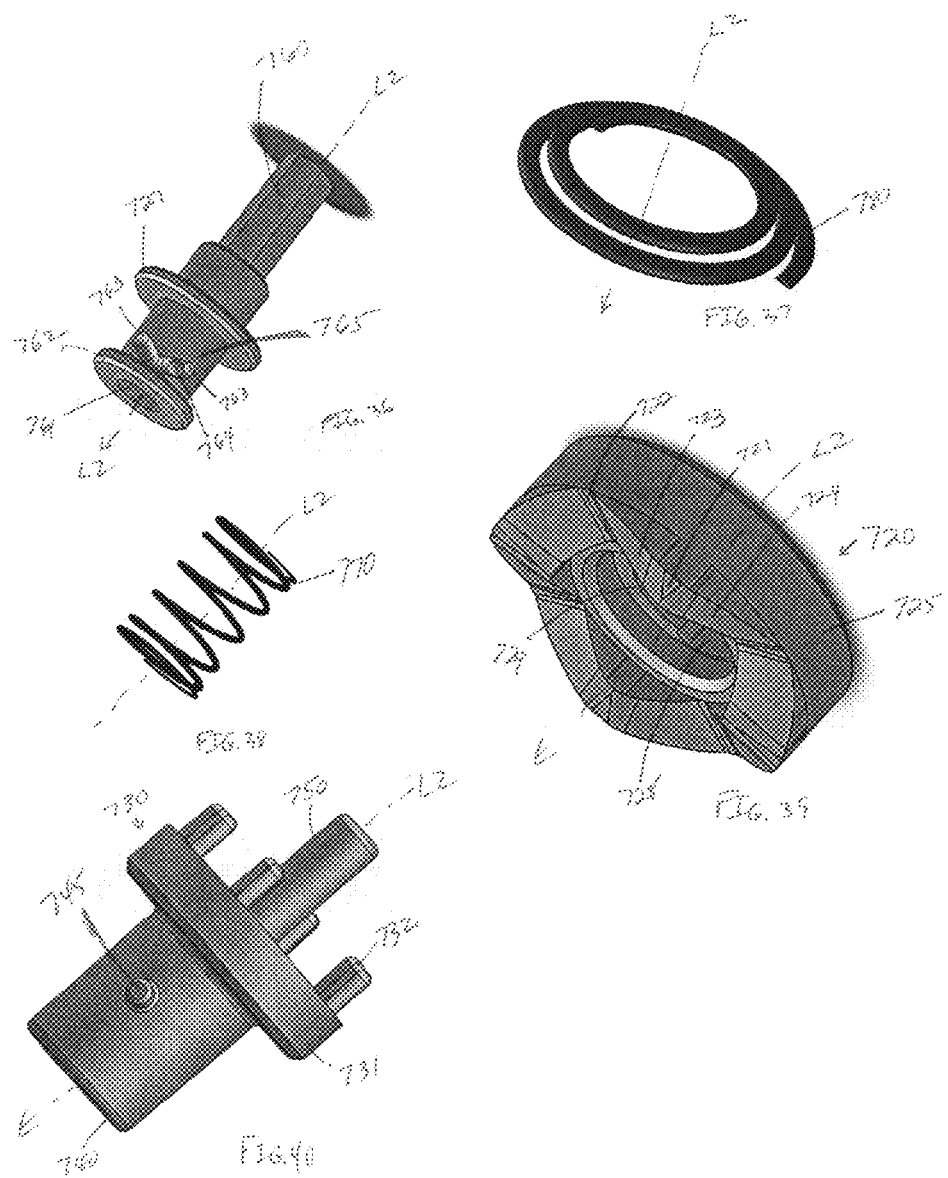

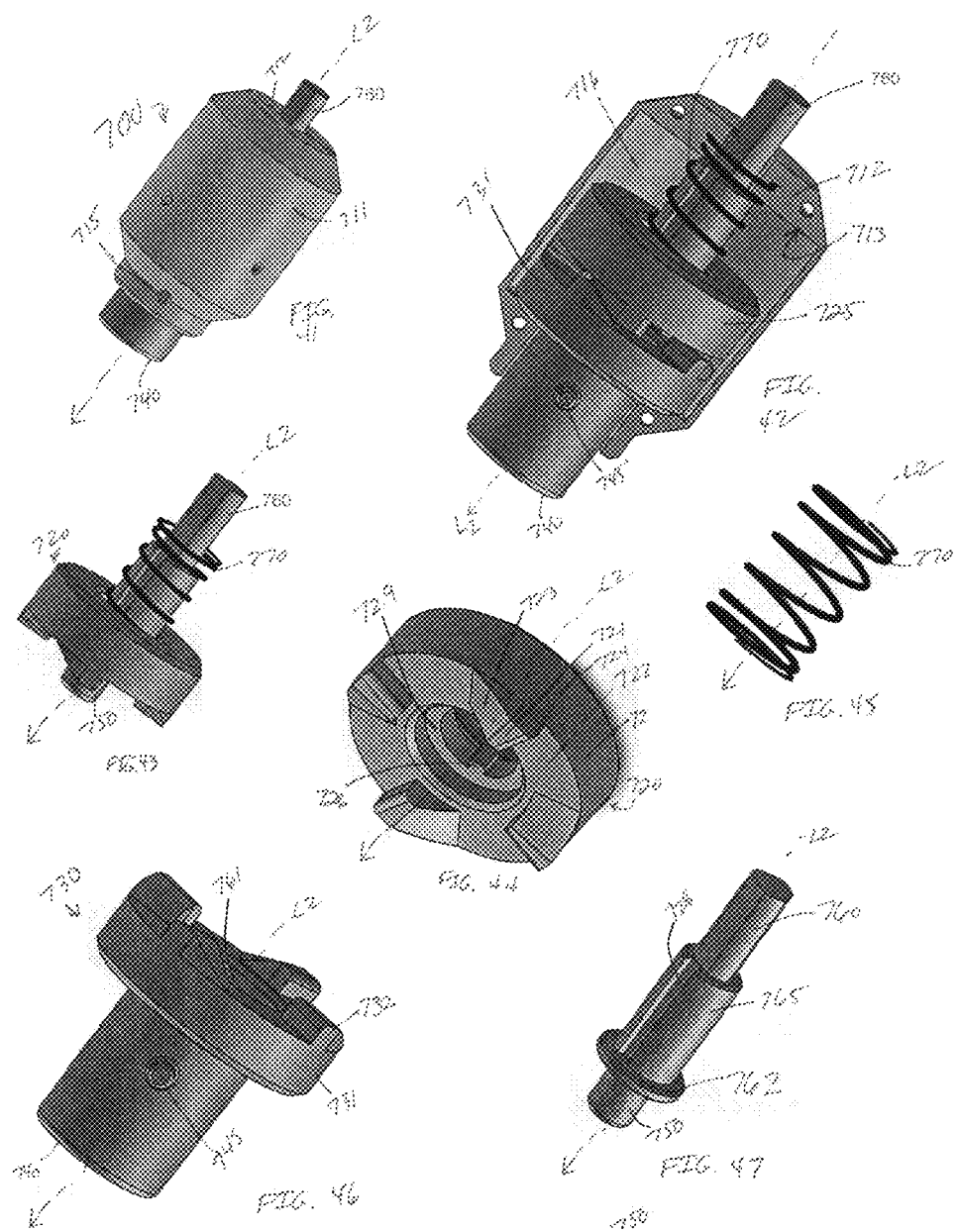

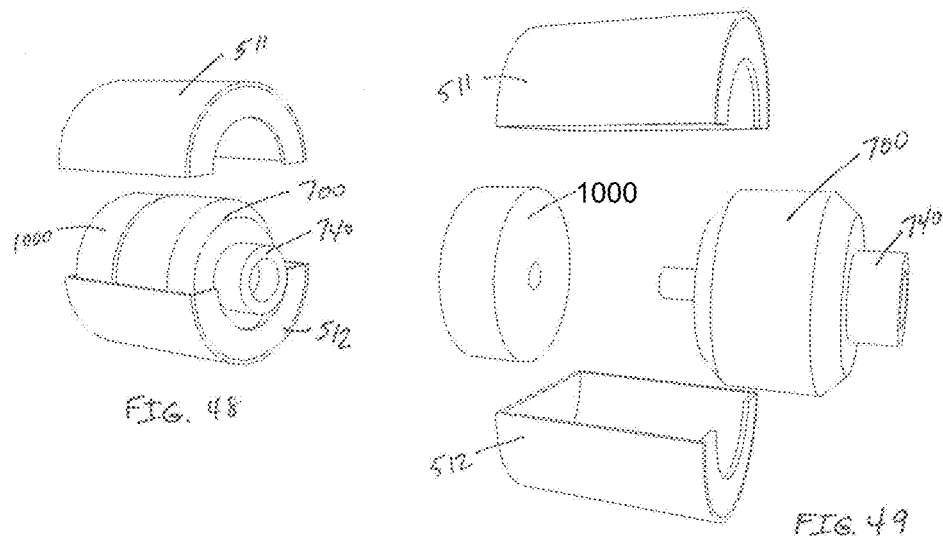
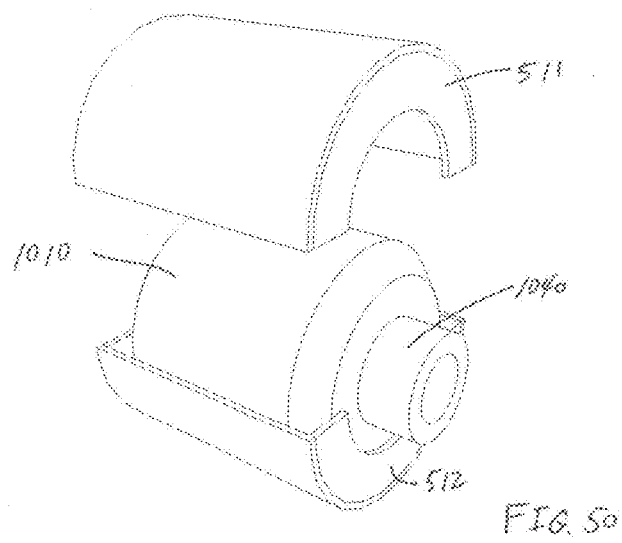

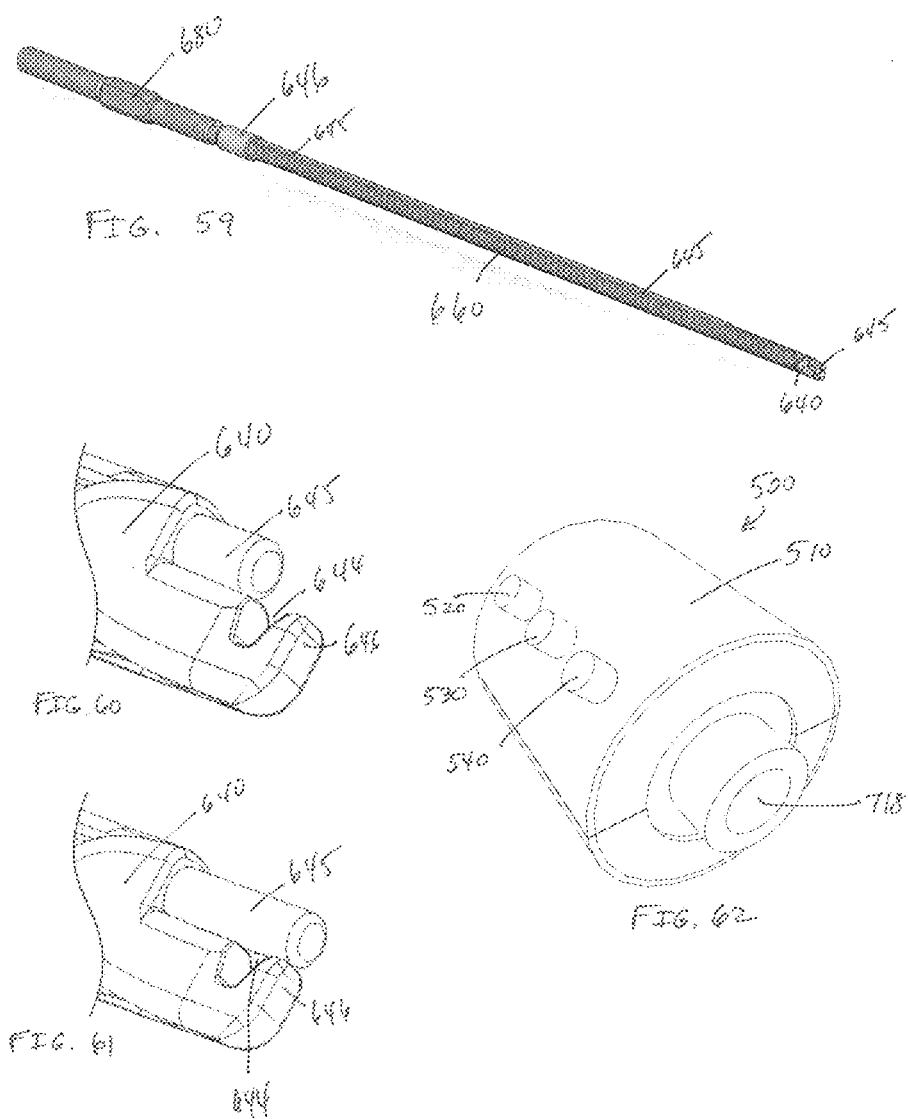

DEVICES, METHODS, AND SYSTEMS TO IMPLANT AND SECURE A FUSION CAGE OR INTERVERTEBRAL PROSTHESIS FOR SPINAL TREATMENT

BACKGROUND

Medical treatment of the spine often involves an injury or disease of an intervertebral disc, the fibrocartilaginous joint between two adjacent vertebrae. Frequently, treatment involves removing the natural disc and fusing the two adjacent vertebrae. A fusion cage frequently is used to promote fusion of two adjacent vertebrae. One or more anchors may be used to secure the cage to one or both of the adjacent vertebrae. In some cases, an intervertebral prosthesis like an artificial disc joint may be used instead of fusing the two adjacent vertebrae. With such prostheses, one or more anchors may be used to secure plates or other components to one or both of the adjacent vertebrae.

The anchors often used to secure a fusion cage or intervertebral prosthesis component to a vertebra may take many forms. For example, a screw may be threaded into a vertebra with the head of the screw holding the treatment device against the vertebra. Nails and other forms of pins also may be used. Generally, the use of such fasteners requires a relatively large incision to accommodate the approach angle needed to adequately insert the screws, nails, or pins through the treatment device and into the vertebra.

SUMMARY

The Applicant of the present application has developed and identified various devices, methods, and systems to secure a fusion cage, a corpectomy implant, or an intervertebral prosthesis component to an adjacent vertebra through a less invasive incision. Examples of such devices, methods, and systems are disclosed in U.S. Pat. Nos. 6,447,546, 8,343,219, 8,617,245, 8,932,359, 9,039,774, and 9,044,337 and U.S. Patent Application Publication Numbers 20130150968, 20140114413, 20150045893, 20150051702, 20150127109, and 20150209089, each of which is incorporated herein by reference. As described in various such publications, for example, a curved, plate-like anchor can be inserted through a relatively narrow incision and then curved through the treatment device to project a tip of the anchor into the adjacent vertebra and secure the treatment device to the vertebra.

In some situations, driving the tip of a plate-like anchor into a vertebra may require significant force. Various devices and methods may be used to supply the force. For example, a punch may be used to transmit an impact from a manually swung hammer through the incision to the end of the anchor. Alternatively, various devices, methods, or systems described in this disclosure may be used.

This application describes various embodiments of devices, methods, and systems that may be used to implant anchors for intervertebral prostheses, cages, and other treatment devices. For example, anchor implantation may be done with an instrument assembly and an impactor assembly. In some embodiments, the instrument assembly may comprise a body having a head, a shaft, and a handle. The instrument assembly may include a retainer to secure the intervertebral prosthesis or intervertebral device to the instrument head. The instrument assembly also may comprise an adjuster for an insertion depth stop.

An impactor assembly may take several forms and each form may have several options. Generally, various embodiments of an impactor assembly will generate impulses for impacting an anchor into a bony segment. For example, the impactor assembly may be powered by a motor. The motor may be energized, for example, electrically, pneumatically, or manually. The motor may comprise a switch, valve, or other mechanism for energizing the motor. The impactor assembly may comprise a transmission for the generating impulses, which may be integral with or separate from the motor. Alternatively or additionally, the motor may directly generate impulses. The impactor assembly may have a bit to engage the anchor. The bit may be removable and also may be selectable from an assortment of differently configured bits adapted for different surgical circumstances.

The impactor assembly may drive the anchor using various techniques and various structures configured to implement such techniques. For example, the tip of the anchor may be advanced into a vertebra using a series of forward impulses applied to the trailing end of the anchor using the impactor assembly. Several variants of this technique may be used. For example, the head of the impactor bit may progress forward unidirectionally. Alternatively, the head of the impactor bit may oscillate, striking the trailing end of the anchor on the forward stroke and retracting from the trailing end of the anchor on the rearward stroke. In another alternative, the anchor also may oscillate with the head of the impactor bit, with the tip of the anchor advancing into the vertebra on the forward stroke and retreating somewhat on the rearward stroke, but with an overall progression of the anchor tip into the vertebra. A damper may be used to moderate the impulses. Other movements of the impactor assembly components may be damped. The force applied to the anchor may range from a mere vibration to a significant translational impulse.

The impactor assembly may have several types of controls. For example, the impactor assembly may provide adjustments of the frequency, displacements, and forces of the impulses delivered to the anchor. The impactor assembly may be configured for manual activation, or alternatively for activation when pressed against an object such as an anchor.

In some situations, a surgeon may want to perforate, score, or otherwise cut a vertebra in preparation for implantation of an anchor in the vertebra. For that, various devices, systems, and alternatives described herein may be used by various methods. For example, a curved knife may be used in place of an anchor. Alternatively, a bit configured with an articulating, sharpened head may be used. Cutting services may be straight, serrated, pointed, or rounded. In some circumstances, a saw-toothed cutting edge or roughened surface may be advantageous. In some situations, a cutting guide may be used in place of the implant during the cutting procedure. The cutting guide may be equipped with hardened surfaces along the cutting tool pathways.

The various devices, systems, and alternatives described herein may be used by various methods. For example, a surgical procedure may use one or more of the following steps: make an incision adjacent to an intervertebral area being treated; remove some or all of the intervertebral disc; determine an appropriate size and configuration for an intervertebral device to be implanted; determine an appropriate size and configuration for one or more anchors to be used to secure an intervertebral device to one or both of the adjacent vertebrae; attach the intervertebral device to an insertion instrument; adjust the instrument to achieve an appropriate depth for insertion of the intervertebral device; insert the intervertebral device into the intervertebral space; place an anchor in a head of the insertion instrument; adjust the frequency, displacement, and force of the impulses to be delivered by the impactor; select an impactor bit appropriate for driving an anchor into one of the adjacent vertebrae; attach an impactor bit to the impactor assembly; connect a head of the bit to a trailing end of the anchor; engage the impactor assembly to drive a tip of the anchor into a vertebrae; remove the impactor assembly; disconnect the insertion instrument from the intervertebral device; remove the insertion instrument from the incision; and close the incision.

If the surgeon wants to perforate, score, or otherwise cut a vertebra in preparation for implantation of the anchor in the vertebra, the surgical procedure may use one or more of the following steps prior to insertion of the anchor: select a knife or cutting head having an appropriate size and configuration; select a bit for the cutting procedure; attach the knife or cutting head to the bit; adjust the frequency, displacement, and force of the impulses to be delivered to the knife or cutting head by the impactor; attach a cutting guide to an insertion instrument; place the cutting guide into the intervertebral space; place the knife or cutting head in a pathway of the cutting guide; engage the impactor assembly to perforate score otherwise cut the vertebral surface; and remove the bit and knife or cutting head from the cutting guide or implant.

BRIEF DESCRIPTION OF THE EXAMPLE VIEWS OF THE DRAWINGS

FIG. 1 depicts embodiments of an intervertebral implant in intervertebral implant anchors placed in an intervertebral space between an upper vertebra in a lower vertebra.

FIG. 2 depicts an embodiment of an intervertebral implant anchor.

FIG. 3 depicts a perspective view of the anchor of FIG. 2 showing a section view taken along indicator line 3-3 of FIG. 2.

FIG. 4 depicts an embodiment of an intervertebral implant.

FIG. 5 depicts a another view of the intervertebral implant of FIG. 4.

FIG. 6 depicts a perspective view of the intervertebral implant of FIGS. 4 and 5 showing a section view taken along indicator line 6-6 of FIG. 4.

FIG. 7 depicts a perspective view of the intervertebral implant of FIGS. 4 and 5 showing a section view taken along indicator line 7-7 of FIG. 5.

FIG. 8 depicts an embodiment of an intervertebral implant and an embodiment of an intervertebral implant anchor.

FIG. 9 depicts the implant and anchor shown in FIG. 8 with the anchor inserted in the implant.

FIGS. 10-15 depict various embodiments of intervertebral implants, anchors, insertion instruments, and anchor impactors.

FIGS. 16-20 depict an embodiment of an insertion instrument and its components.

FIGS. 28-32 depict an embodiment of an impactor transmission assembly and various components thereof.

FIGS. 33-40 depict an embodiment of an impactor transmission assembly and various components thereof.

FIGS. 41-47 depict an embodiment of an impactor transmission assembly and various components thereof.

FIGS. 48-50 depict various schematic representations of various anchor impactor embodiments.

FIGS. 59-61 depict an embodiment of an anchor impactor bit and various components thereof.

FIG. 62 depicts a schematic representation of various components of an embodiment of an anchor impactor assembly.

DESCRIPTION OF VARIOUS EMBODIMENTS AND ALTERNATIVES

Figure 16:
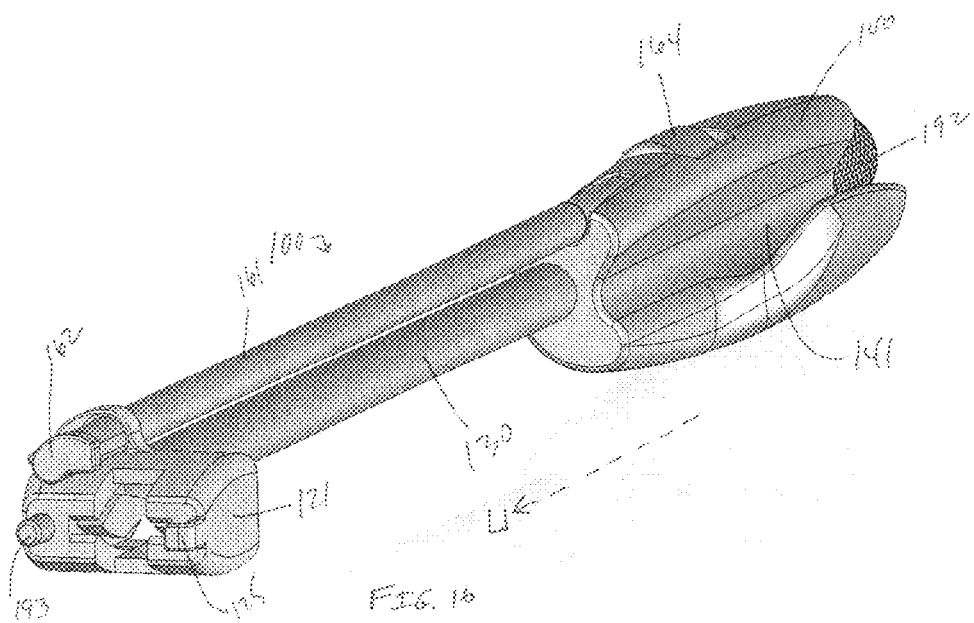

FIG. 1 depicts an exemplary depiction of an intervertebral space between adjacent vertebrae following treatment involving the implantation of a fusion cage. In this depiction, the fibrocartilaginous joint has been removed from the intervertebral space 12 between upper vertebra 10 and lower vertebra 11. Fusion cage 40 has been implanted in intervertebral space 12. Fusion cage 40 is attached to upper vertebra 10 by anchor 70, which is driven through passage 41 in cage 40. Fusion cage 40 is attached to the lower vertebra 11 by anchor 71, which is driven through passage 42 in cage 40.

FIGS. 2 and 3 depict exemplary depictions of an anchor that may be used to fix an intervertebral device to an adjacent vertebra. In this example, anchor 71 has a pair of tips 72, a trailing end 73, a pair of retention catches 74, a pair of insertion stops 75, and an attachment hole 76.

FIGS. 4-7 provide exemplary depictions of a fusion cage. In this example, implant 40 is depicted with sidewall 44. Generally, for example, after placement of a device in intervertebral space 12 as shown in FIG. 1, sidewall 44 preferably will be oriented toward the incision through which implant 40 passes during its placement in intervertebral space 12. In this example, implant 40 configured with upper anchor passage 41 and lower anchor passage 42. As depicted in this example, upper anchor passage 41 extends from sidewall 44 to the top of implant 40, and lower anchor passage 42 extends from sidewall 44 to the bottom of implant 40. For this embodiment, stop surface 45 is provided to abut insertion stop 75 on anchor 71, which limits the transit of anchor 71 through lower passage 42. When tips 72 of anchor 71 are driven fully into lower vertebra 11 as shown in FIG. 1, the abutment of insertion stops 75 against stop surfaces 45 hold implant 40 against lower vertebra 11. This exemplary depiction shows attachment nut 43 disposed on sidewall 44, which in embodiments such as this example might be deployed as a threaded bore configured to mate with a threaded rod to hold the implant to an insertion instrument, for example as depicted in the embodiments of FIGS. 10 and 12.

FIGS. 8 and 9 depict exemplary depictions of some steps that may be used to attach an implant to a vertebra, for example implant 40 to vertebra 11 as shown in FIG. 1. In FIG. 8, anchor 71 is depicted in approach to the entrance to lower passage 42 along sidewall 44. FIG. 9 depicts anchor 71 at the completion of its curvilinear transit of lower passage 42, for example as shown in FIG. 1. In this example, anchor 71 is equipped with two retention catches 74 which may comprise flexible tabs deployed along the sides of anchor 71. During the transit of exemplary anchor 71 through lower passage 42 of exemplary implant 40, catches 74 are compressed against the body of anchor 71, and when such transit is complete catches 74 resile to an extended position and inhibit anchor 71 from backing out of lower passage 42.

FIGS. 10-15 depict exemplary embodiments of systems for treating a spine. In these embodiments, the systems may comprise implant 40, anchor 70, insertion instrument assembly 100, and impactor assembly 500. Impactor assembly 500 depicted in FIGS. 10-11 is electrically powered, impactor assembly 500 depicted in FIGS. 12-15 is pneumatically powered, and impactor assembly 500 depicted in FIG. 15 is powered either electrically or pneumatically. As shown in the embodiments of FIGS. 14-15, impactor 500 may be deployed with easily changeable bits 600.

Figure 17:
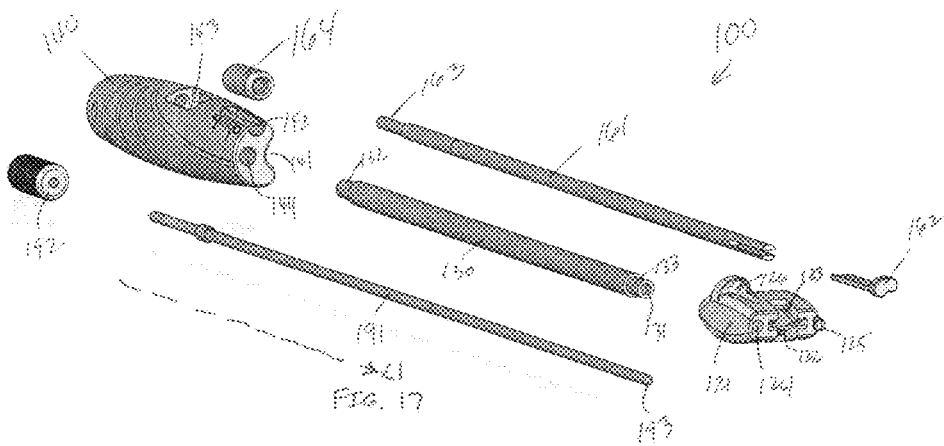
Figures 21, 22:
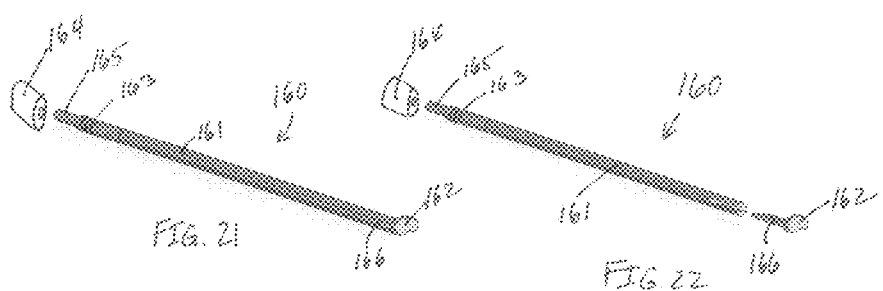
FIGS. 21 and 22 depict an embodiment of an insertion stop assembly and its components.
Figures 23, 24:
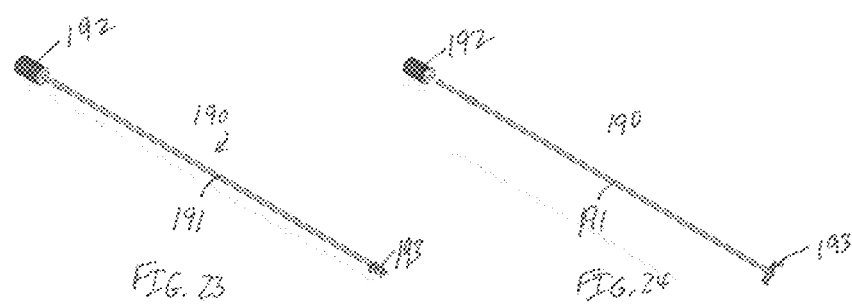
FIGS. 23 and 24 depict an embodiment of an implant retainer assembly and its components.

FIGS. 16-24 depict some exemplary embodiments of an instrument assembly and various components of an instrument assembly. The embodiments of instrument assembly 100 depicted in FIGS. 16-24 may comprise a body assembly 120 (for example as depicted in FIGS. 18 and 19), an insertion stop assembly 160 (for example as depicted in FIGS. 21-22), and a retainer assembly 190 (for example as depicted in FIGS. 23-24). FIG. 17 depicts an exploded view of an instrument assembly 100 and various components of its subassemblies. For the embodiments depicted in FIGS. 16-24, the longitudinal centerline axis of shaft 130, retainer shaft bore 131, retainer shaft 191, and retainer shaft bore 124 generally will be substantially coaxial, and will be substantially parallel to the longitudinal centerline axis of insertion stop shaft 161 and reference axis L1 (examples of which are illustrated in FIGS. 11, 13, 16, and 70).

FIGS. 18-20 depict some exemplary embodiments of the body assembly 120 of the embodiments illustrated in FIGS. 16-17. In this embodiment, body assembly 120 may comprise a head 121, a shaft 130, and a handle 140. This head 121 may comprise upper channel 122, lower channel 123, retainer shaft bore 124, retainer 125, insertion stop bore 126 with offset recess 128, and slots 127 sized and arranged to admit and guide the head of an impactor bit during implantation of the anchors. This shaft 130 may comprise retainer shaft bore 131, handle attachment 132, and head attachment 133. This handle 140 may comprise impactor bit guide 141, insertion stop shaft bore 142, insertion stop knob recess 143, and retainer shaft bore 144. Head 121 is attached to shaft 130 at handle attachment 132, and handle 140 is attached a shaft 130 at head attachment 133. Attachments 132 and 133 may be configured in numerous ways, for example shoulders that pressure fit into corresponding recesses of handle 140 and head 121, respectively, threads that engage corresponding threaded bores of handle 140 and head 121, respectively, or dogs that engage corresponding channels in handle 140 and head 121, respectively.

As depicted in FIGS. 18-20, head 121 is configured and arranged to hold implant 40 during its insertion into intervertebral space 12 and during the insertion of anchors 70 and 71. In this embodiment, head 121 also is configured to guide anchor 71 through lower channel 123 of head 121 into and through lower passage 42 of implant 40 and into lower vertebra 11, and to guide anchor 72 upper channel 122 of head 121 into and through upper passage 41 of implant 40 and into upper vertebra 10. In these embodiments, head 121 may comprise retainer 125, which in these examples may comprise a hook arranged in configured to engage a recess in implant 40, and retainer shaft bore 124, which in these examples allows passage of retainer 193 through head 121 and into a cooperating structure of implant 40 (for example, attachment nut 43 depicted in FIGS. 4, 6, 8, and 9), with retainer shaft 191 transiting retainer shaft bore 131 of shaft 130 and retainer shaft bore 144 of handle 140. In the depicted embodiments, head 121 also may comprise insertion stop bore 126 with offset recess 128, which holds and guides insertion stop assembly 160.

FIGS. 21-22 depict some exemplary embodiments of the insertion stop assembly of the embodiments illustrated in FIGS. 16-17. In these embodiments, insertion stop assembly 160 may comprise shaft 161, head 162 with offset key 166, threading 163, adjusting knob 164, and tail shaft 165. As shown in FIGS. 16-17, for example, assembled shaft 161 may be translatable in insertion stop shaft bore 126 of head 121 and in insertion stop shaft bore 142 of handle 140, with head 162 disposed at one end of shaft 161, and tail shaft 165 disposed at the opposite end of shaft 161. In the embodiments depicted in FIGS. 16-17, for example, an end of shaft 161 with head 162 installed may be placed in insertion stop bore 126 of head 121 with offset key 166 engaged with offset recess 128 of head 121, and the tail shaft 165 located at another end of shaft 161 may be placed in a part of insertion stop shaft bore 142 with threading 163 engaged with threads of adjusting knob 164, which is captured in insertion stop knob recess 143. Head 162 may have a face of suitable size and shape for contacting the surface of a vertebra adjacent to the intervertebral space in which an implant is being inserted. For the illustrated embodiments, for example, head 162 would abut upper vertebra 10 as shown in FIG. 1. When properly adjusted, head 162 would deliver implant 42 the proper insertion depth in intervertebral space 12. In the illustrated embodiments, such adjustment can be achieved by rotating knob 164 on threading 163. Knob 164 resides in insertion stop knob recess 143 of handle 140 when instrument assembly 100 is assembled, and rotating knob 164 on threading 163 translates head 162 along a direction parallel to shaft 130. During this adjustment, a flange 166 on head 162 that extends partially along the exterior of shaft 161 rides in a corresponding offset 128 of insertion stop bore 126 of head 121 to prevent rotation of shaft 161 during adjustment of insertion stop assembly 160. Shaft 161 may be equipped with an indicator of the translation of head 162 with respect to head 121, for example with a line or other mark placed on shaft 121. Adjustment of the insertion depth may be preset or recorded by reference to the position of indicator mark 167 along scale 145.

FIGS. 23-24 depict some exemplary embodiments of the retainer assembly of the embodiments illustrated in FIGS. 16-17. In these embodiments, retainer assembly 190 may comprise shaft 191, actuator knob 192 disposed at one end of shaft 191, and retainer 193 dispose at the opposite end of shaft 191. In these embodiments, knob 192 may be made integral with shaft 191 or may attach to shaft 191 by threadings, flanges, adhesives, fusing, press fitting, or other means. Retainer 193 may, for example, comprise threading compatible with a corresponding threading of attachment nut 43 of implant 40, dogs compatible with a corresponding recess of attachment nut 43 of implant 40, or other means of securely holding implant 40 to head 121. When the depicted embodiments of FIGS. 16-17 are assembled, shaft 191 extends through retainer shaft bore 144 in handle 140, retainer shaft bore 131 of shaft 130, and retainer shaft bore 124 of head 121. To attach implant 40 to head 121 in the embodiments of FIGS. 16-17, for example, implant 40 is placed against the exit face of head 121 with retainer 125 engaged in a recess on one side of implant 40, and retainer 193 extends through bore 124 and into attachment nut 43 of implant 40. The attachment of implant 40 to head 121 may then be completed by rotating shaft 191, which for example tightens in threads of attachment nut 43 if retainer 193 is deployed as a threaded tip or draws down against recesses of attachment nut 43 if retainer 193 is deployed as a dog.

Figures 25, 27:
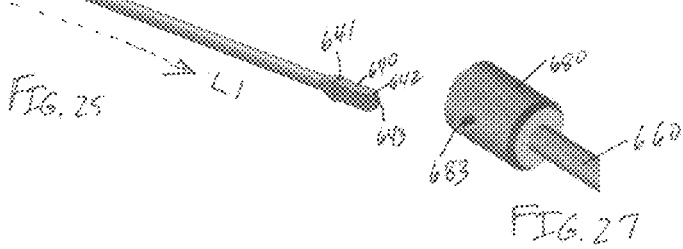

In some of the depicted embodiments, after implant 40 is placed in intervertebral space 12 using instrument assembly 100, anchors 70 and 71 are guided through channels 122 and 123 into passages 41 and 42 and then partially into vertebrae 10 and 11 to a final position as depicted, for example, in FIG. 1. Anchors 70 and 71 may be driven to the final positions manually using a hammer and purpose-built punch or impactor, for example as described in U.S. Pat. Nos. 8,343, 219, 9,039,774, and 9,044,337 and U.S. Patent Application Publication Numbers 20130150968, 20140114413, 20150051702, and 20150209089, each of which is incorporated herein by reference. Preferably, however, anchors 70 and 71 may be driven to the final positions using an impulse impactor assembly, for example using one of the embodiments depicted in FIGS. 10-15. For example as depicted in FIGS. 10-15 and 48-49, an impactor assembly 500 may comprise a bit 600 (for example, as depicted in FIG. 25) and a housing 510 (which may comprise semi-housings, for example half-shells 511 and 512 depicted in FIGS. 48-50) containing a transmission 700 (for example, as depicted in FIG. 28, 33, 41, or 48) and a motor 1000 (for example, as depicted in FIG. 48). Alternatively, a linear drive motor 1010, which may be electrically or pneumatically powered, may be used in various embodiments, some of which may not use a transmission and instead utilize a reciprocating motion generated by the linear drive motor, for example as depicted in FIG. 50, which may be coupled to impactor bit 600 by collet assembly 1040. As another alternative, the internal structure of housing 710 may be formed directly in housing 510, allowing various embodiments to dispense with housing 710. A switch, valve, or other device may be used to energize the motor, for example switch or valve 550 shown in the embodiment depicted in FIG. 54.

Figure 26:
FIGS. 25-27 depict various embodiments of an impactor bit.

In the embodiment depicted in FIGS. 25-27, impactor bit 600 transmits linear impulses from an area proximal to the handle end of insertion instrument 100 to an area proximal to the head end of insertion instrument 100. In the depicted embodiments, bit assembly 600 may comprise head 640, shaft 660, and coupler 680. Head 640 may comprise insertion stops 641, driving recesses 642, and shoulder 643. In some embodiments, coupler 680 may comprise a securing mechanism, for example, threads 681 depicted in FIG. 25, ball detent groove 682 depicted in FIG. 26, or the twist-lock lug 683 depicted in FIG. 27. In some embodiments, coupler 680 may engage the impulse generator (for example, various embodiments of a transmission 700 or a direct drive motor 1010) through a loose or friction fit, or by simple contact with the impulse generator. Generally, embodiments of impactor bit 600 such as those depicted in FIGS. 11, 13, 15 and 25-27 will be deployed during use with the longitudinal centerline axis of shaft 660 substantially parallel to reference axis L1 (for example as shown in FIGS. 11, 13, and 15-17), with head 640 traversing head 121 of the instrument assembly 100 along impactor head slots 127 in the opposite end of shaft 660 traversing impactor bit guide 141 of handle 140.

FIGS. 28-47 depict some exemplary embodiments of transmission assemblies and various components of transmission assemblies. In various depicted embodiments, transmission assembly 700 may comprise a housing 710, for example comprising first shell 711 and second shell 712, a cam assembly 720, a cam follower assembly 730, a collet assembly 740, an arbor shaft 750, a driveshaft 760, and an actuator spring 770.

FIGS. 28-32 depict exemplary embodiments of a transmission for an oscillating impactor. In these embodiments, housing 700 may comprise first housing shell 711 and second housing shell 712 collectively defining a cavity 716 in which cam assembly 720 and cam follower assembly 730 are deployed. As depicted in the embodiments of FIGS. 28-32, cam assembly 720 may comprise cam plate 725, lobe nose 721, lobe heel 722, forward ramp 723, and rearward ramp 724. The cam assembly 720 depicted in FIGS. 28-32 generally will be disposed with a fixed rotational relationship to driveshaft 760. In the illustrated embodiments, cam assembly 720 also may be disposed with a fixed translational relationship to driveshaft 760 in a direction parallel to reference axis L1, for example by being integrally made with driveshaft 760 or by being fully fixed to driveshaft 760, for example by fusing, adhering, or mechanical fastening. Alternatively, cam assembly 720 may be deployed to allow limited translation along driveshaft 760, for example using a key or detent. Rotation of cam assembly 720 in housing assembly 710 may be facilitated by one or more bearings, for example such as bearing 727, which as depicted is configured to reduce friction for both axial and radial loads. Alternatively, separate radial and thrust bearings may be provided, or may be collectively or individually omitted.

The embodiments depicted in FIGS. 28-32 may further comprise cam follower assembly 730 and collet assembly 740. Cam follower assembly 730 may comprises cam follower plate 731 and tappets 732. Generally, a transmission assembly will be deployed with equal numbers of tappets and cam lobes, with each cam lobe being deployed with one nose, one heel, one forward ramp, and one trailing ramp, but other deployments may be advantageous for certain applications. In the embodiments depicted in FIGS. 28-32, cam follower assembly 730 and collet assembly 740 are substantially fixed together with respect to rotational and translational movements, for example by being integrally made or by being fully fixed, for example by fusing, adhering, or mechanical fastening. For the embodiments depicted in FIGS. 28-32, rotation of collet 740 and cam follower assembly 730 in housing 710 is substantially prevented by locator projection 745, which in the depicted embodiments is deployed as a pin disposed in anti-rotation slots 715 formed in first shell 711, which prevents collet 740 and cam follower assembly 730 from rotating while allowing linear translation.

In the embodiments depicted in FIGS. 28-32, cam assembly 720 is deployed at one end of cavity 716 and cam follower assembly 730 is deployed at the opposite end of cavity 716. Alternative embodiments of these and various other embodiments disclosed herein may have the cam assembly and the cam follower assembly positionally reversed, with the drive shaft driving the cam follower assembly and the cam assembly driving the collet. As shown for the embodiments of FIGS. 28-32, transmission assembly 700 comprises a separate arbor shaft 750, which in these embodiments is disposed in arbor shaft pilot hole 761 and a corresponding pilot shaft hole in either cam follower plate 731 or arbor 740. Alternatively, arbor shaft 750 may be integrally formed with cam follower assembly 730, collet assembly 740, or cam assembly 720, as long as cam assembly 720 may rotate with respect to cam follower assembly 730. Alternative embodiments may dispense with an arbor shaft, although use of an arbor shaft generally would tend to enhance the integrity of the spatial relationships between cam assembly 720, cam follower assembly 730, and housing 710, as well as the relative rotational and translational movements of those components.

As shown for the embodiments depicted in FIGS. 28-32, cam assembly 720 and drive shaft 760 are configured to rotate around reference axis L2, while being substantially fixed translationally along axis L2 with respect to housing 710. For these embodiments, cam follower assembly 730 and collet assembly 740 reciprocate translationally along axis L2, while being substantially fixed rotationally about axis L2 due to the deployment of locator projection 745 in anti-rotation slot 715.

An actuator spring may be used to bias the longitudinal displacement of a cam follower assembly within the housing. For the example illustrated in FIGS. 28-32, actuator spring 770 is disposed between cam assembly 720 and cam follower assembly 730 and biases cam follower assembly 730 away from cam assembly 720. In the illustrated embodiments of FIGS. 28-32, tappets 731 are spaced clear of cam noses 721 when cam follower assembly 730 is biased fully away from cam assembly 720, and in this position rotation of cam assembly 720 will not cause any translational movements of cam follower assembly 730. When the exposed end of drive shaft 760 is pressed toward housing 710, cam assembly 720 displaced toward cam follower assembly 730, and with sufficient such displacement, rotation of cam assembly 720 will cause tappets 731 to come into contact with forward ramp 723, nose 721, and trailing ramp 724 and be linearly displaced along reference axis L2. In these embodiments, when housing 710 is held rotationally fixed with respect to insertion assembly 100 and a rotational, pressing force is applied to the end of drive shaft 760, the linear impulses of cam follower assembly 730 along reference axis L2 generated by contact of tappets 732 with forward ramps 723 will be transmitted through collet assembly 740 to bit assembly 600, and then through head 642 to trailing end 73 of an anchor until stops 641 on head 640 contact the proximal end of head 121, thus driving the anchor into its final position in implant 40 and an adjacent vertebra 10 or 11.

FIGS. 33-40 depict additional alternate embodiments of transmission assembly 700. In these embodiments, cam follower assembly 730, collet assembly 740, arbor shaft 750, and housing 710 are configured and deployed similarly to the corresponding structures depicted in FIGS. 28-32. The embodiments of FIGS. 33-40 comprise drive shaft 760 deployed separately from cam assembly 720. In the example depicted in FIG. 36, for example, the drive shaft 760 comprises cam retainer flange 762, shoulder 765, and drive balls 763 deployed in drive ball housings 764. In these embodiments, cam assembly 720 is slidably translatable along shoulder 765 parallel to reference axis L2, with contact of shoulder 729 against cam retainer flange 762 limiting translation in one direction and contact of cam plate 725 with walls 713 limiting translation in the other direction. Drive balls 763 are biased in drive ball housings 764 so that a portion of drive balls 763 are proud of the surface of shoulder 765 with drive balls 763 in the biased position. Such biasing, for example, may be accomplished with springs, resilient plastic, or other elastic structures. In the biased position, the projecting portions of drive balls 763 rest in key ways 728 of cam assembly 720 such that cam assembly 720 rotates with drive shaft 760. Although the depicted embodiments illustrate drive balls, any form of biased key may be used, and the disposition of the biased key and the key way may instead be reversed, with the biased key disposed on cam assembly 720 and the key way disposed on shoulder 765 of drive shaft 760. For these embodiments, when cam assembly 720 experiences sufficient resistance against cam follower assembly 730, drive balls 763 overcome their biasing force and are forced into drive ball housings 764, allowing cam assembly 722 to rotate around reference axis L2 with respect to drive shaft 760, thus providing a form of dampening action.

The embodiments depicted in FIGS. 33-40 may also have additional dampening structures. For example, the depicted embodiments comprise damping spring 780 disposed between cam assembly 720 and end walls 713 of housing 710. In these embodiments, biasing spring 780 generally will allow cam assembly 722 to oscillate translationally along drive shaft 760 in the direction of reference axis L2 while maintaining engagement of noses 721 with tappets 732. Such oscillation of cam assembly 720 will dampen the impulses delivered to collet assembly 740. In these embodiments, the biasing force delivered by damping spring 780 and the biasing force exerted against drive balls 763 can be coordinated to provide a dampening action such that the desired impulse profile is delivered to collet assembly 740.

FIGS. 41-47 depict additional embodiments of transmission assembly 700. In these embodiments, collet assembly 740 and cam follower assembly 730 are substantially rotationally and translationally fixed with respect to housing 710. For example, anti-rotation slot 715 in first shell 711 of housing assembly 710 may be configured with internal dimensions substantially conforming to the exterior dimensions of locator projection 745, with collet assembly 740 rotationally and translationally fixed to cam follower assembly 730, for example as described above. In the depicted embodiments, drive shaft 760 comprises cam retainer flange 762 and shoulder 765, in which key way 728 extends longitudinally parallel to reference axis L2. Depicted drive shaft 760 also comprises arbor shaft 750, which may be made integrally with shaft 760 or attached to shaft 760. In the depicted embodiments, drive shaft 760 and arbor shaft 750 are substantially fixed translationally along reference axis L2 with respect to housing assembly 710.

In the exemplary embodiments depicted in FIGS. 41-47, cam assembly 720, for example, may comprise nose 721, heel 722, forward ramp 723, rearward ramp 724, cam plate 725, cam key 726, and shoulder 729. Cam assembly 720 in these embodiments may translate bidirectionally along shoulder 765 in the direction of reference axis L2, and such translation may be limited, for example, in one direction by the contact of cam retainer flange 762 with shoulder 729 and in the other direction by the contact of cam plate 725 with walls 713 of housing 710. Although the inter-fitting of cam key 726 and key way 728 in these embodiments permit such translation, such inter-fitting substantially prevents rotation of cam assembly 720 on drive shaft 760 around reference axis L2. Alternatively, key 726 may be disposed along shoulder 765, and key way 728 may be disposed on cam assembly 720. In these embodiments, for example, actuator spring 770 assists such translation of cam assembly 720 in the forward direction and inhibits such translation of cam assembly 720 in the rearward direction, thus enhancing engagement of the cam lobes of cam assembly 720 with tappets 732 of cam follower assembly 730. The cam lobes on cam assembly 720 and tappets 732 may, for example, be configured to generate an impulse at collet assembly 740 when forward ramp 723 contacts tappet 732. Those components also may, for example, be configured to generate an impulse by contact of nose 721 with follower plate 731 during the relative rotation of cam assembly 720 with respect to cam follower assembly 730, or to generate an impulse by contact of tappet 732 against heel 722 during such relative rotation, or to generate an impulse by both such actions. Regardless, in the depicted embodiments, the profiles of nose 721, heel 722, forward ramp 723, rearward ramp 724, and tappet 732 may be tailored to produce the desired impulse forces at collet assembly 740.

The profiles of the impulses generated and delivered by transmission assembly 700 may be adjusted and tailored in additional ways. For example, hydraulic tappets may be used to dampen the impulse that the tappets deliver to the cam follower plate. Alternatively, resilient tappets or noses may be used to dampen the impulses. A dampening action may also be promoted through the use of a viscous hydraulic fluid in cavity 716, with the impulse forces being tailored by the size of the clearance of the reciprocating internal components (for example cam follower assembly 730 or cam assembly 720, depending on the embodiment) to the internal walls of the cavity, by the size of ports in the reciprocating internal components, by valves in the reciprocating internal components, or by other structures or arrangements that allow the flow of the hydraulic fluid through or around the reciprocating internal components. Of course, the spring coefficients of any actuator or dampening springs also may be selected to tailor the impulse forces. The rotational speed of the drive shaft generally will also affect the impulse profile.

In various embodiments, transmission assembly 700 may be deployed separately from motor 1000, for example instead of deploying transmission assembly 700 and motor 1000 together in a housing 510, some embodiments of which are depicted in FIGS. 48-49. FIGS. 51-55, for example, depict various exemplary embodiments and related components for systems that deploy transmission assembly 700 independently. In the example depicted in FIGS. 51-54, a transmission assembly 700 deployed for use with a detachable motor 1000 is shown. In these embodiments, for example, driveshaft 760 may extend from the housing a sufficient distance such that gripping driveshaft 760 with a drill chuck is convenient. In these examples, driveshaft 760 is driven rotationally with respect to housing 710 without translating relative to housing 710. Follower plate 731 may be held stationary in housing 710 (which in this example comprises half shells 711 and 712), for example by retainer pin 733. In these embodiments, cam plate 725 rotates with driveshaft 760, for example being driven by keys 726 (which may be integral with or attached to driveshaft 760) riding in corresponding keyways 728 of cam plate 725, and cam plate 725 reciprocates linearly along driveshaft 760. Alternatively, the structures of follower plate 731 may be formed in housing 710.

Figure 51:
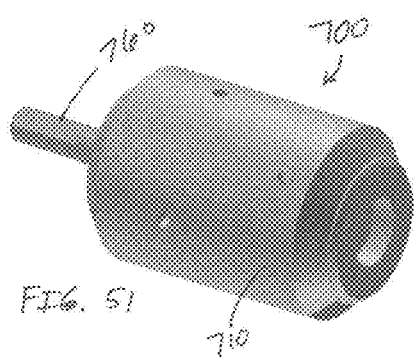
FIGS. 51-53 depict an embodiment of an impactor transmission assembly and various components thereof.
Figure 52:
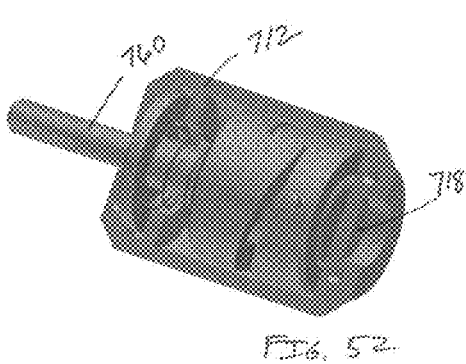
Figure 53:
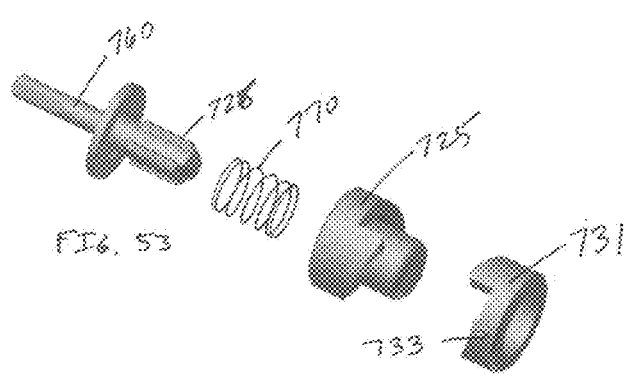
Figure 54:
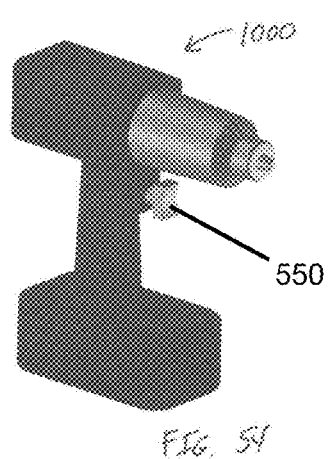
FIG. 54 depicts an embodiment of a motor for powering an impactor transmission.
Figure 55:
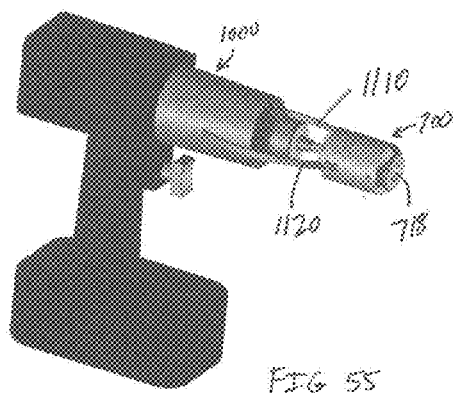
FIG. 55 depicts an embodiment of a motor and transmission combination.

The various embodiments depicted in FIGS. 51-53 maybe driven by various means. For example, FIGS. 54-55 depict an exemplary embodiment in which transmission assembly 700 is powered by a surgical drill 1000. In the example shown in FIG. 55, rotation of transmission assembly 700 with respect to drill 1000 is inhibited by locating arms 1110 and 1120, which may be deployed in a number of ways. In the depicted example, locating arms 1110 and 1120 comprise spring steel bands attached to housing 710 and drill 1000. In another of many alternatives, locating arms may be made integrally with drill 1000 or housing 710, and inter-fit recesses or attachments on the other component.

In various embodiments, housing 510 or housing 710 may be deployed with an interface for bit 600 that allows the impactor assembly to dispense with collet assembly 740. For example, the embodiments of FIGS. 51, 52, and 55 deploy a bit interface 718. These examples, bit interface 718 is configured as a recess surrounded by shoulder injury which bit head 680 may be located when an anchor impacting operation is in progress. The bit may reside in interface 718 loosely or by friction fit. Similar structures may also, for example, be deployed on housing 510. Alternatively, collet assembly 740 may also be deployed with a bit interface employing a loose or interference fit for bit 600.

Figure 56:
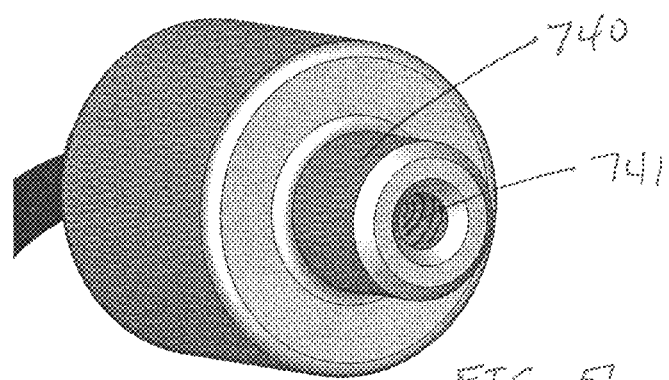
FIGS. 56-58 depict various embodiments of impactor transmission components.
Figure 57:
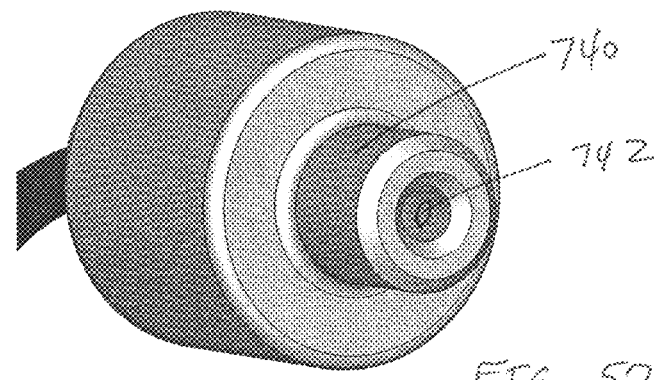
Figure 58:
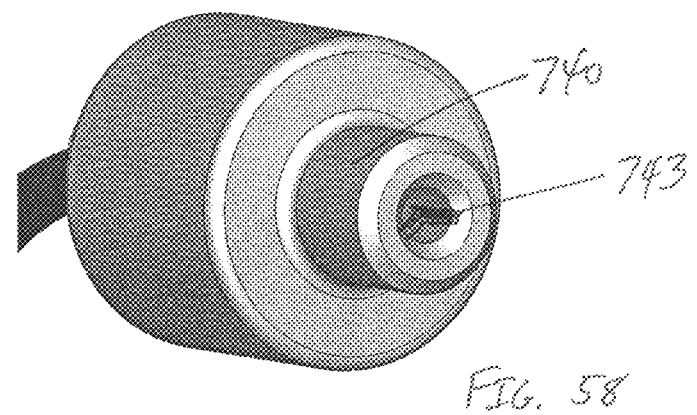

In various alternatives, bit 600 may be secured to collet 740, housing 710, or housing 510 by various alternatives, some of which are depicted in FIGS. 56-58. In FIG. 56, for example, threading 741 may be deployed to inter-fit with threading 681 on coupler 680 of bit 600, for example as depicted in FIG. 25. In FIG. 57, for example, ball detent 742 may be deployed to engage detent groove 682 on coupler 680 of bit 600, for example as depicted in FIG. 26. In FIG. 58, for example, recess 743 may be deployed to engage lug 683 on coupler 680 of bit 600, for example as depicted in FIG. 27. Deployments of projections and recesses may, of course, be reversed; for example, a ball detent may be deployed on collet 740, housing 710, or housing 510 to engage a ball detent recess deployed on coupler assembly 680, or a twist-lock lug may be deployed on collet 740, housing 710, or housing 510, to engage a corresponding recess deployed on coupler assembly 680.

Various embodiments in which the bit is connected to a collet 740, housing 710, or housing 510 may be used in deployments where it is desired that the anchor oscillate with the head of the impactor bit, with the tip of the anchor advancing into the vertebra on the forward stroke and retreating somewhat on the rearward stroke, but with an overall progression of the anchor tip into the vertebra. Alternatively, the bit may have a loose or interference fit with collet 740, housing 710, or housing 510, and be urged in a direction opposite to the impact direction by a resilient force, for example a spring, torsion bar, or hydraulic strut. Various configuration of bits 600 may be used where it is desired that the anchor oscillate with ahead of the impactor bit. For example, the embodiment depicted in FIGS. 59-61 allows anchor 70 or 71 to be connected to bit 600 and receive bidirectional oscillating forces. In this example, bit 600 comprises shaft 660 having coupler 680 disposed at one end and head 640 disposed at the other end. In this embodiment, head 640 comprises gate 644, which in this example is formed as a recess creating pin 646, and anchor lock 645, which in this example is formed as a rod extending parallel to shaft 660. In this example, anchor 70 or 71 (for example, as depicted in FIGS. 2-3) may be coupled to bit 600 by placing the anchor in gate 644 with pin 646 protruding through attachment hole 76 of the anchor while lock 645 is refracted and gate 644 is open, followed by capturing the anchor in gate 644 when lock 645 is advanced and gate 644 is closed. In this embodiment, such attachment of an anchor will cause the anchor to reciprocate with bit 600. Various structures may be used to control the advancement and retraction of lock 645. For example, the embodiment depicted in FIG. 59 comprises knob 646, which when rotated into a first position retracts lock 645 and when rotated into a second position advances lock 645 and locks it into place close gate 644.

In some embodiments, it may be desirable to control the frequency, displacement, or force of the impacts delivered by the impactor assembly. In the embodiment depicted in FIG. 62, for example, impactor assembly 500 comprises frequency adjustment 520, displacement adjustment 530, and force adjustment 540, which may be used to adjust the frequency, displacement, or force of the impacts delivered by the impactor assembly. In various embodiments, these controls may be omitted, deployed individually, or deployed in any combination.

Numerous methods may be used to treat a spine using various embodiments of the implants, anchors, instrument assemblies, and impactor assemblies described above. For example, a treatment method may comprise one or more of the following steps: make an incision adjacent to an intervertebral area being treated; remove some or all of the intervertebral disc; determine an appropriate size and configuration for an intervertebral device to be implanted; determine an appropriate size and configuration for one or more anchors to be used to secure an intervertebral device to one or both of the adjacent vertebrae; attach the intervertebral device to an insertion instrument; adjust the instrument to achieve an appropriate depth for insertion of the intervertebral device; insert the intervertebral device into the intervertebral space; place an anchor in a head of the insertion instrument; adjust the frequency, displacement, and force of the impulses to be delivered by the impactor; select an impactor bit appropriate for driving an anchor into one of the adjacent vertebrae; attach an impactor bit to the impactor assembly; connect a head of the bit to a trailing end of the anchor; engage the impactor assembly to drive a tip of the anchor into a vertebrae; remove the impactor assembly; disconnect the insertion instrument from the intervertebral device; remove the insertion instrument from the incision; and close the incision.

If the surgeon wants to perforate, score, or otherwise cut a vertebra in preparation for implantation of the anchor in the vertebra, the surgical procedure may use one or more of the following steps prior to insertion of the anchor: select a knife or cutting head having an appropriate size and configuration; select a bit for the cutting procedure; attach the knife or cutting head to the bit; adjust the frequency, displacement, and force of the impulses to be delivered to the knife or cutting head by the impactor; attach a cutting guide to an insertion instrument; place the cutting guide into the intervertebral space; place the knife or cutting head in a pathway of the cutting guide; engage the impactor assembly to perforate score otherwise cut the vertebral surface; and remove the bit and knife or cutting head from the cutting guide or implant.

Exemplary embodiments of such spinal treatment methods may use some or all of various devices and systems described above. For example, a fusion cage such as implant 40 depicted in FIGS. 4-9 may be used with anchor 70 and anchor 71 such as the embodiment depicted in FIGS. 2, 3, 8, and 9. For such embodiments, implant 40 is attached to head 121 of instrument 100 by hooking retainer 125 into one side of implant 40 and screwing retainer 193 into attachment nut 43. Insertion stop 160 may be adjusted using knob 164, and instrument 100 is used to insert implant 40 into intervertebral space 12 until insertion stop head 162 contacts vertebra 10. The frequency, displacement, and force of the impulses to be delivered by the impactor assembly 500 may be adjusted using frequency adjustment 520, displacement adjustment 530, and force adjustment 540. Generally, the impulses may have a frequency greater than 1 hertz, but generally less than 80 hertz and preferably between 4.3 and 36.6 hertz, with impact force ranging from 0.2 to 100 Newtons and energy per impact ranging between 0.02 to 5 Joules. Exemplary pneumatic embodiments may have an operating pressure between 40-140 PSI, preferably around 100 PSI. A consumption in various pneumatic embodiments may be between 180 to 400 liters per minute, Impactor bit 600 may be selected such that the dimensions and layout of bit head 640 (for example, the size and locations of stops 641, recesses 642, shoulder 643, gate 640, and lock 645) correspond with the dimensions and layout of instrument head 121 (for example, the size and locations of channels 122 and 123 and impactor head slot 127) and the dimensions and layout of anchors 70 and 71 (for example, the size and locations of trailing ends 73, catches 74, and attachment holes 76). Coupler 680 and collet 740 are connected, for example using threadings 681 and 741, detent groove 682 and ball detent 742, or lug 683 and recess 743.

Continuing this example, anchor 70 is placed in upper channel 122 and connected to head 640 of impactor bit 600, for example by simple contact of trailing end 73 with recess 642 and shoulder 643, or by bidirectional connection using gate 644, lock 645, and attachment hole 76. Impactor assembly 500 may be actuated to transmit impulse forces from bit 600 to anchor 70, until the tip of anchor 70 is driven through lower passage 42 to the appropriate position in vertebra 10 with insertion stops 75 abutting stop surfaces 45. Head 640 may be disengaged from anchor 70. Anchor 71 is placed in lower channel 123 and connected to head 640 of impactor bit 600, for example by simple contact of trailing end 73 with recess 642 and shoulder 643, or by bidirectional connection using gate 644, lock 645, and attachment hole 76. Impactor assembly 500 may be actuated to transmit impulse forces from bit 600 to anchor 71, until the tip of anchor 71 is driven through upper passage 41 to the appropriate position in vertebra 11 with insertion stops 75 abutting stop surfaces 45. Head 640 may be disengaged from anchor 71. The impactor assembly 500 may then be removed and the insertion instrument 100 may be disconnected from intervertebral device 40 by rotating knob 192 and removing retainer 193 from attachment nut 43. Insertion instrument 100 may be removed from the incision, and the incision closed.

After appreciating this disclosure, those of skill in the art will recognize that the steps of the various methods, processes, and other techniques disclosed herein need not be performed in any particular order, unless otherwise expressly stated or logically necessary to satisfy expressly stated conditions. In addition, after appreciating this disclosure those skilled in the art will recognize that the invention may be embodied in a variety of different forms of devices and systems, and that various changes, substitutions, and alterations can be made without departing from the spirit and scope of the invention. References herein to surfaces or other structures as "upper," "top," "lower," and "bottom" are generally arbitrary and for convenience only, and those of skill in the art will recognize after appreciating this disclosure that such designations appropriately may be reoriented in particular embodiments. The described embodiments are illustrative only and are not restrictive, and the scope of the various inventions are defined solely by the following claims and any further claims in this application or any application claiming priority to this application.

The invention claimed is:

1. A system for treating a joint between two bony segments comprising:
   an implant configured for placement in the joint;
   an anchor configured to retain the implant along one of the bony segments;
   an elongated insertion instrument comprising a head disposed at one end of the instrument, the head comprising an implant retainer disposed at a first end of the head, a channel configured to receive the anchor along a second end of the head and direct the anchor into the implant at the first end of the head, and a guide configured to receive a head of an impactor bit; and
   an anchor impactor comprising an impactor bit, the impactor bit comprising a bit coupler and a head, and an impulse generator comprising a housing defining a central axis, a collet reciprocatable along the central axis and comprising a collet coupler configured to connect with the bit coupler, a follower translatable along the central axis and comprising a follower plate and a tappet projecting above a surface of the follower plate, a cam rotatable about the central axis and comprising a cam plate and a cam lobe projecting above a surface of the cam plate, a driveshaft rotatable about the central axis, and a spring disposed between the cam and the follower and biasing the cam and the follower apart.

2. The system of claim 1 in which the collet, the follower, the cam, and the driveshaft are disposed collinearly along the central axis.

3. The system of claim 2 further comprising a motor comprising a motor shaft rotatable about the central axis.

4. The system of claim 3 in which the driveshaft and the motor shaft are integral.

5. The system of claim 1 further comprising an arbor shaft on which the cam is disposed and rotatable, and wherein the follower is translatable through engagement with the cam.

6. The system of claim 1 in which the cam lobe comprises a nose, a heel, a forward ramp, and a rearward ramp.

7. The system of claim 6 in which the cam and the follower have a first impact configuration in which the follower is in contact with the nose of the cam and a second impact configuration in which the follower is in contact with the heel of the cam.

8. The system of claim 1 in which the cam is coupled to and reciprocatable with the collet.

9. The system of claim 1 in which the cam is fixed to and rotatable with the driveshaft.

10. The system of claim 9 in which the cam is translatable along and rotatable with the driveshaft.

11. The system of claim 10 in which the cam and the follower have a first configuration in which rotation of the cam causes the cam lobe to contact the follower, and a second configuration in which the cam is rotatable without contact between the cam lobe and the follower.

12. The system of claim 1 comprising plural tappets and plural cam lobes, with the number of tappets equal to the number of cam lobes.

13. The system of claim 1 comprising plural tappets and plural cam lobes, with the number of tappets not equal to the number of cam lobes.

14. The system of claim 1 in which the tappet is hydraulic.

15. The system of claim 1 in which the housing comprises a cavity in which the cam and the follower are disposed, and the cavity is filled with hydraulic fluid.

16. The system of claim 15 in which the cavity comprises ports configured to restrict a flow of the hydraulic fluid.

17. The system of claim 1 in which the cam is coupled to the driveshaft by a biased key, with the biased key having an engaged position in which the cam is constrained to rotate with the driveshaft and a released position in which the cam is rotatable with respect to the driveshaft.

18. A method of treating a joint between two bony segments comprising the steps of:

acquiring a system for treating a joint between two bony segments as recited in claim 4;

inserting the implant into the joint by using the elongated insertion instrument;

placing the anchor into the implant;

connecting the impulse generator to the impactor bit;

adjusting a first control to set a selected frequency of impulses generated by the impact generator, adjusting a second control to set a selected displacement of impulses generated by the impact generator, and adjusting a third control to set a selected force of impulses generated by the impact generator;

energizing the impulse generator to produce impulses at the head of the impactor bit; and driving a tip of the anchor into one of the bony segments by applying impulses to an opposite end of the anchor with the head of the impactor bit.

19. The method of claim 18 further comprising the steps of configuring the impulse generator and impactor bit to cause the anchor to oscillate with the head of the impactor bit, and applying impulses to the anchor such that the tip of the anchor advances into said bony segment on a forward stroke of the impactor bit and retreats on a rearward stroke of the impactor bit, but with an overall progression of the tip of the anchor into said bony segment.

* * * * *

UNITED STATES PATENT AND TRADEMARK OFFICE
CERTIFICATE OF CORRECTION

PATENT NO.         : 10,258,479 B2
APPLICATION NO.    : 14/827297
DATED              : April 16, 2019
INVENTOR(S)        : Stewart et al.

Page 1 of 1

It is certified that error appears in the above-identified patent and that said Letters Patent is hereby corrected as shown below:

In the Claims

In Column 16, Line 21, in Claim 18, delete "claim 4;" and insert --claim 1;-- therefor Signed and Sealed this
Fifth Day of May, 2020

Andrei Iancu
*Director of the United States Patent and Trademark Office*